Figure 1:
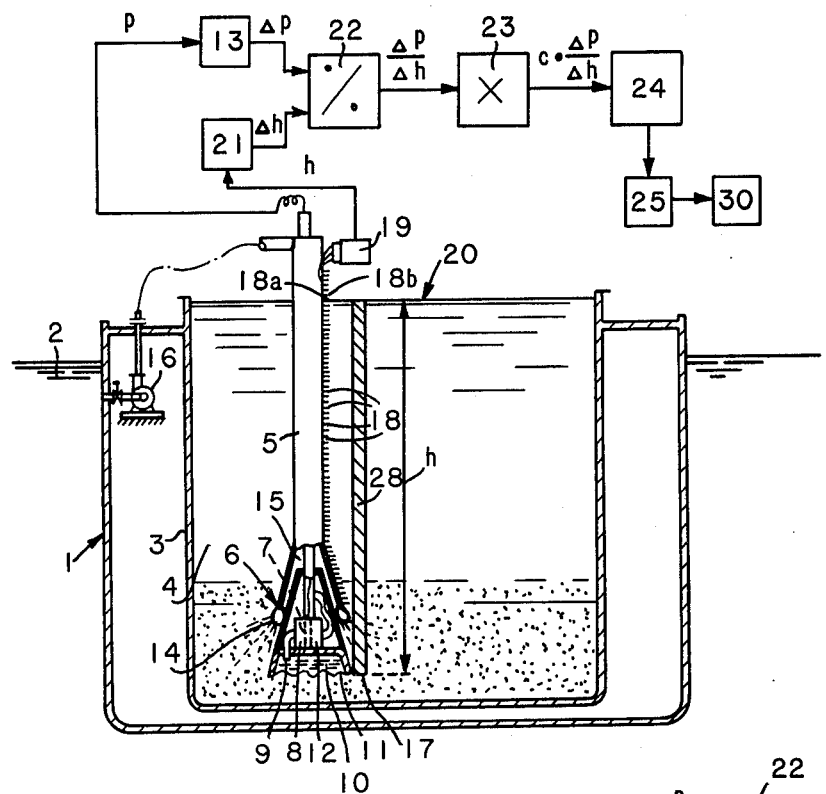

United States Patent [19]

van der Veen

[11] 4,438,651

[45] Mar. 27, 1984

[54] METHOD AND DEVICE FOR MEASURING THE DENSITY OF FLUIDS PARTICULARLY DREDGINGS

[76] Inventor: Romke van der Veen, No. 87, van Boetzelaerlaan, 2581 AD The Hague, Netherlands

[21] Appl. No.: 306,958

[22] Filed: Sep. 30, 1981

[30] Foreign Application Priority Data

Oct. 9, 1980 [NL] Netherlands .......................... 8005603

[51] Int. Cl.³ .............................................. G01N 9/00
[52] U.S. Cl. ........................................ 73/433; 73/438
[58] Field of Search ................ 73/433, 434, 438, 32 R

[56] References Cited

U.S. PATENT DOCUMENTS

| | | | |
|---|---|---|---|
| 3,190,126 | 6/1965 | Wright | 73/438 |
| 3,690,180 | 9/1972 | van der Veer | 73/438 |
| 4,169,377 | 10/1979 | Scheib | 73/304 R |
| 4,195,527 | 4/1980 | Ebeling et al. | 73/434 |
| 4,252,097 | 2/1981 | Hartford et al. | 73/438 |

FOREIGN PATENT DOCUMENTS

| | | |
|---|---|---|
| 1323340 | 2/1963 | France . |
| 2250985 | 6/1975 | France . |
| 7900161 | 7/1980 | Netherlands . |

*Primary Examiner*—James J. Gill
*Attorney, Agent, or Firm*—Diller, Ramik & Wight

[57] ABSTRACT

The density r of a fluid, e.g. dispersion or suspension, is measured in a plurality of steps and by calculating the same according to the formula $r = c \times dG/dV$, wherein c is a constant value and $dG/dV$ is the differential of the weight measuring value $dG$ to the volume measuring value $dV$. In this way some measuring inaccuracies of the measuring instruments can be avoided.

3 Claims, 5 Drawing Figures

METHOD AND DEVICE FOR MEASURING THE DENSITY OF FLUIDS PARTICULARLY DREDGINGS

The invention relates to a method for measuring the density of a fluid contained in a holder, particularly the density of dredgings, in which the density is derived from volume measuring values and weight measuring values.

In this method considerable measuring errors are introduced, which are inherent in the measuring device to be employed in said method. The measuring accuracy strongly depends on the variation of the shift of the zero point measuring value, which will be clarified hereinafter with reference to formulae. The density $r = c \times G/V$, wherein c represents, in principle, a constant value, G is the weight and V is the volume of the fluid to be measured. The term "fluid" is to be understood to mean herein a normal liquid, consisting of one or more kinds of liquid or a mixture of different liquids, which may or may not be relatively soluble, or a suspension of a liquid and a solid substance. The term "weight measuring value" is to denote a measuring value depending on weight. A weight measuring value may, for example, consist of a pressure measuring value concerning the pressure at the lower end of a measuring column of the liquid and likewise the volume measuring value may consist of a height measuring value concerning the height of a measuring column of the fluid.

In practice it appears that the proportionality factor c in the commerically available pressure sensors and column height sensors remains substantially constant, so that by calibrating the measuring device it can be accurately assessed during the execution of the measuring method with a calibrating fluid, the density of which is known. The inaccuracy of these measurements is mainly due to the fact that the density measuring signal $r = c_o + r \times P/h$, wherein $c_o$ is, in principle, a constant which can be eliminated by a zero point shift during calibration. Virtually this so-called constant $c_o$ appears to be anything but constant. The variation of the $c_o$ is so great, so unpredictable and so poorly reproducible that the resultant measuring data become impermissibly inaccurate.

The invention has for its object to provide a method in which adverse effects on the measuring accuracy due to unassessible, unintentional and hence unaccountable zero point shifts are avoided. For this purpose in at least two different states $t_n$ and $t_{n+1}$ during measurements carried out on different fluid layers to be metered, for example, at two different instants during loading of the holder, weight measuring values $G_n$ and $G_{n+1}$ and volume measuring values $V_n$ and $V_{n+1}$ are measured, and for the state difference $dt = t_{n+1} - t_n$ the differential $dG/dV$ of the weight measuring value dG to the volume measuring value dV is calculated and the density r is calculated by multiplication of said differential by the constant value c determined by filling the holder with a calibration fluid, for example, water of known density $r_1$ during a calibration measurement and by subsequently calculating the constant value c from the product of the known density $r_1$ and the differential $dV_1/dG_1$ of the volume measuring value $V_1$ to the weight measuring value $G_1$, expressed in a formula: $r = c \times dG/dV$, wherein $c = r_1 \times dV_1/dG_1$. This calculation of the density based on measured differential values is fully independent of the zero point value $c_o$ and unassessible variations thereof.

The measuring accuracy is enhanced by repeated calculation of the density $r_n$ from the differential $dG_n/dV_n$ of the weight measuring value $G_n$ to the volume measuring value $V_n$ measured substantially in the same period and by deriving the mean density R of the fluid in the holder by averaging the arithmetic value $r_n$ for the density r.

In particular averaging is carried out by regression analysis.

The invention furthermore relates to and provides a device for measuring the density of a fluid in a holder by the method embodying the invention, said device comprising volume measuring means for measuring the fluid volume to be metered, weight measuring means for measuring the weight of the fluid volume to be metered and arithmetic means for calculating the density from the measuring values obtained from the volume measuring means and the weight measuring means, said device being characterized according to the invention by an arithmetic unit connected to the volume measuring means and to the weight measuring means for calculating the difference $dG/dV$ of the weight measuring value dG to the volume measuring value dV and by a multiplier coupled with the arithmetic unit and a memory storing the constant value c for providing an arithmetic value for the density $r = c \times dG/dV$.

A device embodying the invention suitable for use in the rough dredging business comprises a plurality of fluid sensors disposed at different known levels in the holder.

In order to eliminate a source of errors due to the presence of packed-up sand or other solids preferably the weight measuring means comprise at least one pressure sensor disposed below in the holder with a water inlet disposed at said place and ensuring the fluidisation state of the fluid.

Figure 2:
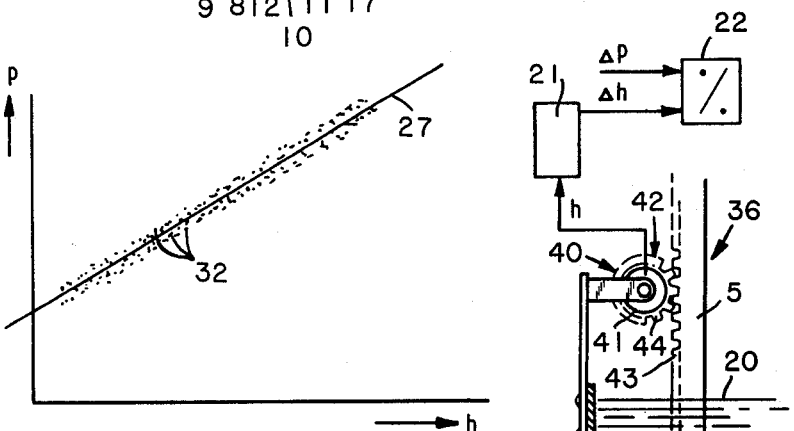
Figure 5:
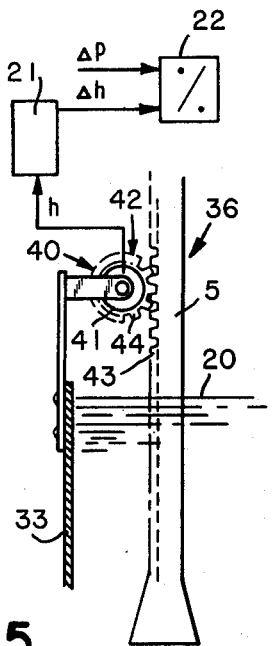
Figure 3:
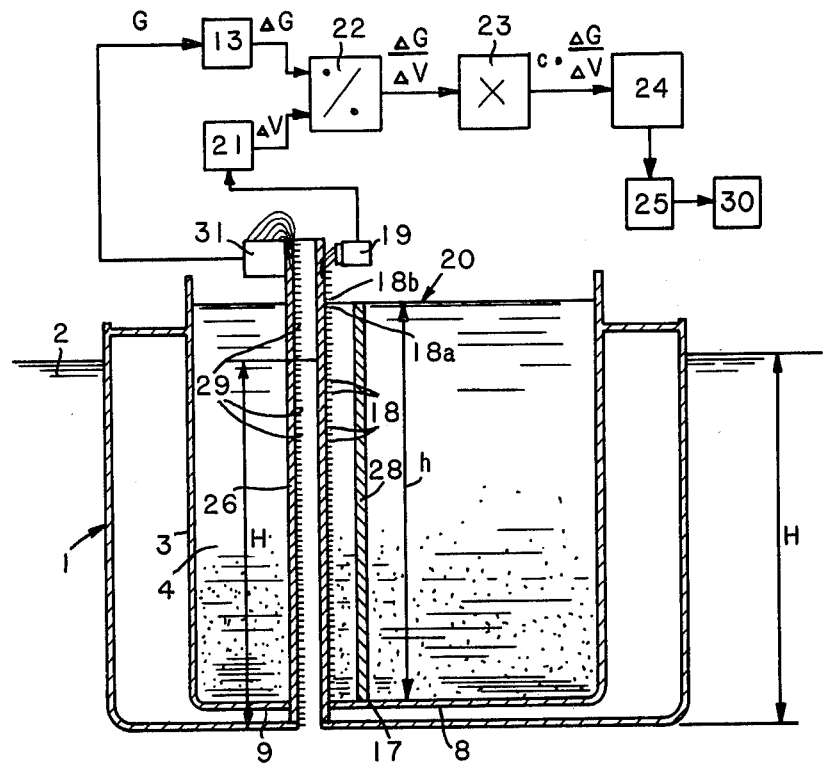
Figure 4:
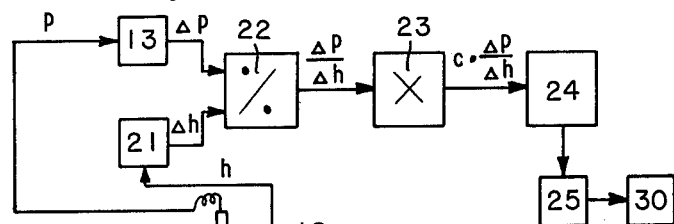
Figure 4:
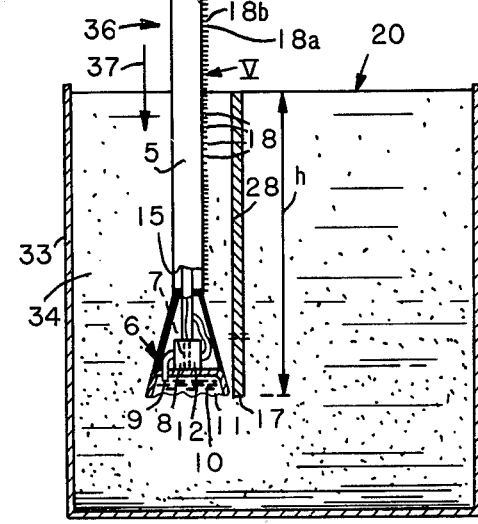

The invention will be described more fully hereinafter with reference to a drawing. The drawing shows schematically in:

FIG. 1 a cross-sectional view of a dredger comprising a device embodying the invention with the circuit diagram, FIG. 2 is a graph of measuring values, FIGS. 3 and 4 each a cross-sectional view like FIG. 1 of a holder with different variants of the device embodying the invention, and FIG. 5 a variant of detail V of FIG. 4. A dredger 1 floating on water 2 comprises a hold 3 for receiving dredgings 4 consisting of, for example, a mixture of water, sludge and sand. During filling of the hold 3 the density r of the mixture is repeatedly measured. For this purpose the dredger 1 is provided with a measuring device comprising a measuring tube 5. At the lower end of the measuring tube 5 a pressure difference sensor 6 comprising measuring means for measuring the pressure P at the lower end 17 of a dredgings column 28 is arranged, a measuring diaphragm 7 of which bounding a measuring chamber 8, which communicates through a channel 9 with a fluid chamber 10, the bottom of which is formed by a flexible diaphragm 11. The pressure beneath the diaphragm 11 is thus picked up by the pressure difference sensor 6, which applies a voltage proportional to the pressure difference between the pressure in the measuring chamber 8 and the atmospheric pressure prevailing in the other chamber 12 to a differentiator 13. The measured presssure difference is equal to the weight of the dredgings column 28 standing above the diaphragm 11. On the outer side of the measuring tube 5, directly above the lower end of said measuring tube 5 water inlets 14 are provided, which are fed with water through a duct 15 by a water pump 16 and which ensure that the dredgings above the diaphragm 11 remain in a fluidisation state.

The measuring device according to the invention furthermore comprises column height measuring means for measuring the height of the dredgings column h. These column height measuring means comprise a large number, for example, hundred relatively insulated electrodes 18, which are disposed in known, preferably equal, small height differences one above the other and which form level sensors and are connected by separate, electric conductors to a column height sensor 19, which indicates by the highest electrode 18a already present below the dredgings level 20 and hence short-circuited by earth that the measuring column height h extends in between said electrode 18a and the electrode 18b disposed directly above the former. In this way with a repetitive rate of, for example, 10 times a second, a pair of associated measuring values is picked up, i.e. $P_n$ and $h_n$ relating to the then present dredgings column 28. The sensor 19 is connected to a differentiator 21, which like the differentiator 13 each time differentiates the incoming signal, which means that each time the differentials dh and dP relating to the two consecutive pair of measuring signals $P_n$ with $h_n$ and $P_{n+1}$ with $h_{n+1}$ are assessed, said differentials dh and dP being applied to a divider 22 for calculating $$dP/dh = \frac{P_{n+1} - P_n}{h_{n+1} - h_n}.$$

After multiplication of this quotient in a multiplier 23 by a factor c, the instantaneous, calculated density r, $r = c \times dP/dh$ is applied to a memory 24. An arithmetic unit 25 is calculates the mean value R of the density values r stored in the memory 24. Preferably said arithmetic unit 25 is constructed in the form of a regression analyser which calculates the mean value R according to the formula of the "smallest squares". By adding an index i to the measured values covering a range from 1 to n, n representing the total number of assessments at a given instant, R can be directly calculated by the following formula:

$$R = c \times \frac{\Sigma P_i h_i - \frac{\Sigma P_i \Sigma h_i}{n}}{\Sigma h_i^2 - \frac{(\Sigma h_i)^2}{n}}$$

When again an assessment has been made ($P_{n+1}$ and $h_{n+1}$) R changes according to the following calculation:

$$R = c \times \frac{(\Sigma P_i h_i + P_{n+1} h_{n+1}) - \frac{(\Sigma P_i + P_{n+1})(\Sigma h_i + h_{n+1})}{n+1}}{(\Sigma h_i^2 + h_{n+1}^2) - \frac{(\Sigma h_i + h_{n+1})^2}{n+1}}$$

R is the slope of the line 27 of FIG. 2, which is a graph of the measuring points 32 determined by measuring values $h_n$ and $P_n$. The result will be that after n points, when loading is completed, R is the best imaginable approximation of the number which is proportional to the density r in the hold 3. This regression analysis is superior to the determination of the average of all slopes from point to point, since in this case the average slope will finally be the line of connection between the first and the last point of assessment. However, all points are considered to have arbitrary errors and by starting from the average slopes the errors at the first and the last point have too great an effect. In the linear regression the slope is found which fits best to all points and the errors at said points are all taken into account in the same manner.

The output of the arithmetic unit 25 is connected to an indicator or a recorder 30.

By this method and this device the density r of the dredgings 4 in the hold 3 can be accurately assessed, even when the dredgings level 20 is fluctuating due to backwash of the dredger 1.

FIG. 3 corresponds with FIG. 1, the difference being, however, that as a weight measuring value $G_n$ the immersion depth H of the dredger 1 is chosen rather than a pressure measuring value $P_n$. The immersion depth H is measured at a riser 26 preferably arranged centrally in the dredger 1 and communicating with the outboard water 2. Inside said riser 26 a sequence of electrodes 29 are arranged at small, equal level intervals and connected through electric conductors to a weight sensor 31. The sequence of electrodes 18 (FIG. 1) are arranged on the outer side of the tube 26 and provided a column measuring value relating to the height of the measuring column 28 or in other terms relating to the volume V of the fluid contained in the hold 3.

Particularly if it is intended to measure the quantity of solids in the hold, it is unimportant whether the sand of the dredgings has partly settled or not. Fluidisation of a dredgings column is then not necessary. This measuring method is particularly suitable in filling a stationary vessel by means of an adjacent earth suction dredger.

FIG. 4 corresponds with FIG. 1, but the invention is applied here to a holder 33 formed by a tank rather than to a dredger, said holder containing a different fluid 34, for example, crude oil having light and heavy constituents. A density sensor 36, comprising a tube 35 is immersed in the direction of the arrow 37 gradually further into the fluid, whilst in various immersion states $t_n$ and $t_{n+1}$ weight and immersion depth measurements are carried out. For this purpose at the lower end of the tube 35 a pressure e.g. a difference sensor 6 (FIG. 1) is arranged and at the side of the tube a sequence of fluid sensors 18 are connected to a column sensor 19.

FIG. 5 shows another device 40 for measuring immersion depth changes dh, with which at a constant level 20 of the fluid the downward displacement dh of the density sensors between the states $t_n$ and $t_{n+1}$ is measured, which downward displacement is measured e.g. by a measuring device 41, which is coupled with the driving mechanism 42 of the density sensor 36. This driving mechanism 42 comprises a rack clip 43 with a pinion 44.

What I claim is:

1. A method of measuring the density of a fluid contained in a holder, particularly the density of dredgings, in which the density is derived from volume measuring values and weight measuring values, characterized in that in at least two different states $t_n$ and $t_{n+1}$ during measurements carried out on different fluid layers to be metered, for example, at two different instants during loading of the holder weight measuring values $G_n$ and $G_{n+1}$ and volume measuring values $V_n$ and $V_{n+1}$ are measured, that for the state difference $dt = t_{n+1} - t_n$ the differential dG/dV of the weight measuring value dG to the volume measuring value dV is calculated and that the density r is calculated by multiplication of said differential by the constant value c determined by filling the holder with a calibration fluid, for example, water of known density $r_1$ during a calibration measurement and by subsequently calculating the constant value c from the product of the known density $r_1$ and the differential $dV_1/dG_1$ of the volume measuring value $V_1$ to the weight measuring value $G_1$, expressed in a formula: $r = c \times dG/dV$, wherein $c = r_1 \times dV_1/dG_1$.

2. A method as claimed in claim 1, characterized in that repeatedly the density $r_n$ is each time calculated from the differential $dG_n/dV_n$ of the weight measuring value $G_n$ to the volume measuring value $V_n$ measured substantially in the same period and that the mean density R of the fluid contained in the holder is derived by averaging the arithmetic values $r_n$ for the density r.

3. A method as claimed in claim 2, characterized in that averaging is carried out by regression analysis.

* * * * *